United States Patent [19]
Fry

[11] Patent Number: 6,132,982
[45] Date of Patent: Oct. 17, 2000

[54] OLIGOSACCHARIDE AMINO ALDITOLS AND ASSAY METHOD

[75] Inventor: Stephen Charles Fry, Edinburgh, United Kingdom

[73] Assignee: Novo Nordisk A/S, Bagsvaerd, Denmark

[21] Appl. No.: 09/043,439

[22] PCT Filed: Sep. 23, 1996

[86] PCT No.: PCT/GB96/02351

§ 371 Date: Mar. 18, 1998

§ 102(e) Date: Mar. 18, 1998

[87] PCT Pub. No.: WO97/11193

PCT Pub. Date: Mar. 27, 1997

[30] Foreign Application Priority Data

Sep. 22, 1995 [GB] United Kingdom .................. 9519393

[51] Int. Cl.[7] .................. G01N 33/573; G01N 33/53; G01N 33/531; C12Q 1/00; C07H 1/00
[52] U.S. Cl. .................. 435/7.4; 435/4; 435/7.1; 435/975; 435/961; 536/1.11; 436/543
[58] Field of Search ................. 435/7.1, 7.4, 975, 435/961, 4; 436/543; 536/1.11

[56] References Cited

U.S. PATENT DOCUMENTS

| | | |
|---|---|---|
| 4,563,421 | 1/1986 | Habenstein et al. . |
| 4,716,101 | 12/1987 | Thompson et al. . |
| 5,258,295 | 11/1993 | Starr et al. . |

FOREIGN PATENT DOCUMENTS

| | | |
|---|---|---|
| 0 176 246 | 4/1986 | European Pat. Off. . |
| 0387875 | 9/1990 | European Pat. Off. . |
| 0 536 939 | 9/1992 | European Pat. Off. . |
| 2 183 832 | 6/1987 | United Kingdom . |
| WO 90/05304 | 5/1990 | WIPO . |

OTHER PUBLICATIONS

Fry et al. Curr. Top. Plant Biochem. Physiol. 11: 42–62, 1992.
Fanutti et al. Planta 200: 221–228, 1992.
Fry SC. Biochem. Soc. Symp. 60: 5–14, 1994.
Fry et al. Symp. Soc. Exp. Biol. 44: 285–298, abstract, 1990.
Redgwell et al. Plant Physiol. 103: 1399–1406, 1993.
Sipe et al. J. Biol. Chem. 266: 8002–8007, abstract, 1991.
Sulova et al. Anal. Biochem. 229: 80–85, Jul. 1995.
Goldman et al. Eur. J. Biochem. 227: 372–378, 1995.
Nishitani et al. J. Biol. Chem. 267: 21058–21064, abstract, 1992.
Dakour et al. Anal. Biochem. 204: 210–214, 1992.
Potter et al. Plant Physiol. 103: 235–241, 1993.
Fry et al., "An unambiguous nomenclature for xyloglucan–derived oligosaccharides", *Physiologia Plantarum*, vol. 89, pp. 1–3, May 1993.
Fry et al., "Xyloglucan endotransglycosylase, a new wall–loosening enzyme activity from plants", *Biochemical Journal*, vol. 282, pp. 821–828, Jan. 1992.

*Primary Examiner*—James C. Housel
*Assistant Examiner*—S. Devi
*Attorney, Agent, or Firm*—Howson and Howson

[57] ABSTRACT

Disclosed is a method of detecting the presence of a compound of interest (such as an enzyme), or the spatial distribution within a sample of a compound of interest. The method comprises the step of impregnating or coating a suitable base material with a marker substance capable of reacting or interacting with the compound of interest, the marker substance being labeled in a detectable manner (for example fluorescently, radioactively or being colored) and having a substantially different affinity for the base material than the product of the reaction or interaction thereof with the compound of interest. The method further comprises the steps of bringing the impregnated base material into contact with the sample under test, to permit the labeled marker substance to react or interact with any target compound present in the sample, removing either unreacted labeled marker substance or labeled reacted product with a suitable solvent, and detecting the presence of labeled marker substance remaining on the base material, or detecting the liberation of labeled reacted product from the base material, to give an indication of the presence or absence of the compound of interest. The marker substance may be an oligosaccharide, oligosaccharidyl-1-amino-1-deoxy-alditols (OADs) being particularly preferred. A method of manufacturing OADs is also disclosed.

9 Claims, No Drawings

OLIGOSACCHARIDE AMINO ALDITOLS AND ASSAY METHOD

The invention relates to methods for locating and measuring the activities of compounds such as enzymes, e.g. glycosylhydrolases (enzymes that catalyse the hydrolysis of glycosidic linkages), transglycosylases (enzymes that catalyse transglycosylation), and lyases (enzymes that catalyse the eliminative cleavage of glycosidic linkages).

Living organisms possess a wide variety of glycosylhydrolase and transglycosylase enzymes, which play numerous diverse roles in the lives of the organisms by acting on carbohydrate substrates including xyloglucan, other hemicelluloses, cellulose, starch, glycogen, chitin and pectic polysaccharides. Laboratory methods for detecting and measuring these enzymes usually employ aqueous solutions of appropriate substrates placed in vessels (such as test tubes), which are monitored for enzyme-catalysed changes e.g. by colorimetric, radiochemical, chromatographic or viscometric methods.

However, such methods tend to be time-consuming and do not readily lend themselves to the screening of numerous samples of the enzymes. In addition, the methods do not readily provide spatial information on the distribution or localisation of the enzymes within a specimen such as a gel electrophoretogram or part of an organism.

In one aspect, the present invention provides a method of detecting the presence of a compound of interest, or the spatial distribution within a sample of a compound of interest, the method comprising the step of impregnating or coating a suitable base material with a marker substance capable of reacting or interacting with the compound of interest, the marker substance being labelled in a detectable manner (for example fluorescently, radioactively or being coloured) and having a substantially different affinity for the base material than the product of the reaction or interaction with the compound of interest, the method further comprising the steps of bringing the impregnated base material into contact with the sample under test to permit the labelled marker substance to react or interact with any target compound present in the sample, removing either unreacted labelled marker substance or labelled reacted product with a suitable solvent, and detecting the presence of labelled marker substance remaining on said base material, or detecting the liberation of labelled reacted product from said base material, to give an indication of the presence or absence of the compound of interest.

The invention exploits the ability of some carbohydrates but not others to bind to the base material in the chosen solvent.

Preferably, the compound of interest is an enzyme, and the marker substance is a substrate for the enzyme. Said substrate for the enzyme may be a protein, a peptide, a polysaccharide or an oligosaccharide. In a particularly preferred method, the substrate is an oligosaccharidyl-1-amino-1-deoxy-alditol. These compounds have been developed by the applicants and are believed to be new in themselves. They are referred to where appropriate in this specification as "OADs", which term is to be taken to include O-glycosyl-1-amino-1-deoxy-alditols, O-oligoglycosyl-1-amino-1-deoxy-alditols, O-glycosyl-6-amino-6-deoxy-aldonic acids, O-oligoglycosyl-6-amino-6-deoxy-aldonic acids and/or their lactones, and related products of reductive amination.

It may in some cases be an advantage that the reducing carbohydrate not only possesses one reducing site but possesses two or more reducing sites randomly placed in said reducing carbohydrate. These additional reducing sites may be obtained with an oxidation agent such as sodium periodate.

The invention also provides a method of manufacturing OADs involving the reaction of a reducing carbohydrate with an ammonium salt and a reducing agent. Preferably, the ammonium salt is ammonium hydrogencarbonate and the reducing agent is sodium cyanoborohydride. Further preferred features of the invention are described in the subsidiary claims.

As stated above the method of the invention may be used for detecting enzyme activity and/or for detecting the spatial distribution within a sample of an enzyme. In particular (but not exclusively) the method of the invention may be used for the following enzymes: transglycosylases such as dextransucrase, amylosucrase, inulosucrase, glycogen phosphorylase, starch phosphorylase, xylan synthase, glucan synthase, pectin synthase, glycogen synthase, starch synthase, callose synthase, chitin synthase; glycosylhydrolases (endoacting) such as xylanase, endoglucanase, chitinase, mannanase, polygalacturonase, β-amylase, arabinanase, galactanase, rhamnogalacturonase; lyases such as pectin/pectate lyase, alginate lyase; glycosylhydrolases (exoacting) such as α-amylase, amyloglucosidase, α-L-arabinofuranosidase, α-D-galactosidase, β-D-galactosidase, β-D-glucosidase, α-L-fucosidase, β-D-mannosidase, α-D-mannosidase, exo-polygalacturonase, N-acetyl-β-D-glucosaminidase, α-D-xylosidase.

A specific embodiment of the invention will now be described by way of example. The enzyme to be tested for in this example is xyloglucan endotransglycosylase (XET) [ref 1].

1. Preparation of Labelled oligosaccharide

The reducing oligosaccharide 4-O-[4-O-[4-O-[6-O-α-D-Xylopyranosyl-β-D-glucopyranosyl]-6-O-(2-O-β-D-galactopyranosyl)-α-D-xylopyranosyl-β-D-glucopyranosyl]-6-O-(2-O-β-D-galactopyranosyl)-α-D-xylopyranosyl-β-D-glucopyranosyl]-D-glucose ("XLLG", using the abbreviated nomenclature of ref 2) (1 gram) is dissolved in 25 ml of a saturated aqueous solution of ammonium hydrogencarbonate containing 1 gram of sodium cyanoborohydride ($NaCNBH_3$) and incubated in the dark at 25° C. for 7 days to permit reductive amination. The ammonium hydrogencarbonate is then removed by drying, and the (ninhydrin-reactive) aminated derivative of XLLG is purified e.g. by gel-permeation chromatography or cation-exchange chromatography. The product is believed to be an oligosaccharidyl-1-amino-1-deoxyalditol, i.e. a derivative of XLLG in which the reducing terminal D-glucose moiety has been replaced by 1-amino-1-deoxy-D-glucitol.

The oligosaccharidyl-1-amino-1-deoxyalditol (50 mg) is dissolved in 3 ml of 3% borax (di-sodium tetraborate; pH=9.0–9.5) and a freshly-prepared solution of 10 mg lissamine rhodamine sulphonyl chloride [purchased from Molecular Probes Inc., USA] in 0.75 ml of dry dimethylformamide (DMF) is added gradually, with stirring, and the mixture is incubated in the dark overnight. A further 0.75 ml of DMF containing 10 mg lissamine rhodamine sulphonyl chloride is added and the mixture incubated for a further 8 h. The bright pink oligosaccharidyl-1-amino-1-deoxyalditol-lissamine-rhodamine conjugate (referred to as XLLGol-SR) is purified by gel-permeation chromatography followed by reversed-phase chromatography on a $C_{18}$-silica gel column. After washing of the latter column with water, a methanol gradient is applied and the XLLGol-SR elutes in about 50% methanol.

2. Preparation of xyloglucan-impregnated Paper

Whatman No. 1 filter paper is moistened with a 1% aqueous solution of xyloglucan and dried. The XLLGol-SR preparation is diluted into enough 75% aqueous acetone to give an absorbance at 580 nm ($A_{580}$) of 0.2; the xyloglucan-coated sheet of Whatman No. 1 paper is then dipped through this solution and re-dried; the product is referred to as "XET-paper". Suitably sized pieces (e.g. 72×108 mm) of the XET-paper may then be glued with a non-aqueous adhesive onto a non-absorbent medium such as a sheet of transparent acetate.

3. Conduct of Assay (a) Dot-blot Test for XET Activity in Aqueous Solutions (i) The source (e.g. the stem of a growing plant) to be tested for XET activity is homogenised in a suitable buffer such as 250 mM succinate, pH 5.5, containing 10 mM calcium chloride and 10 mM dithiothreitol, and the homogenate is centrifuged to give a clear supernatant. Other samples that might be tested for XET activity include fractions eluted from a chromatography column, samples of spent culture media from plant cell suspension culture, or samples of XET that have been treated with substances whose effect on XET activity are to be investigated.

(ii) A spot of each enzyme solution is pipetted on to a marked position in a piece of XET-paper. If the spots are 4 $\mu$l, the spacing between the samples can conveniently be 9 mm (centre-to-centre, i.e. as in a standard 96-well test plate format).

(iii) The XET paper is then quickly (before the spots have dried) clamped between two sheets of plastic (e.g. acetate sheets, as used on overhead projectors) and incubated e.g. at 20° C. for 1 hour.

(iv) The incubated XET-paper and its plastic backing is then placed (paper-side down) in a dish containing about 150 ml of a solvent [e.g. freshly prepared ethanol/formic acid/water (1:1:1 by volume)] that will remove from the paper the unreacted XLLGol-SR but not any XLLGol-SR that has become incorporated into the xyloglucan owing to XET-catalysed transglycosylation. The paper now readily detaches from the plastic backing.

(v) The paper is then rinsed in running water for 5 minutes, then in approximately 100 ml of acetone for 5 minutes, and then dried thoroughly. If desired, drying can be expedited by a 5-minute treatment in an oven at 80° C.

(vi) The paper is then examined under a short-wavelength ultraviolet lamp (e.g. emitting at 254 nm; suitable eye- and skin-protection should be worn). Active XET is indicated by a pink (orange-fluorescing) spot, which can be quantified, e.g. by use of a scanning spectrofluorimeter. The assay method is useful for testing for the presence of substances that promote or inhibit XET activity.

(b) Activity Printing, e.g. to Localise XET Activity within Plant Tissue or an zymograms The XET-paper is buffered, e.g. by spraying with 500 mM succinate, pH 5.5, containing 10 mM calcium chloride and 10 mM dithiothreitol. The plant tissue is sliced to produce an exposed surface; for mapping XET activity over the surface area of a leaf, it may be beneficial to press the leaf between the test paper and a rough surface (e.g. sandpaper) or to press the leaf on the test paper under a very cold (eg –80° C.), heavy flat metal place (which is subsequently allowed to reach room temperature) to promote tissue disruption. The exposed tissue surface, or a gel electrophoretogram, or other surface in which XET activity is to be mapped, is then pressed on to the damp paper for about 1 minute so that the enzyme is transferred on to the paper. The enzyme source is then removed from the XET-paper, and steps (iii) to (vi), above, are performed.

The above example illustrates the invention as applied to a transglycosylase enzyme, XET. The method is also applicable to the assay of glycosylhydrolase enzymes. For example, Whatman No. 1 paper that has been impregnated with XLLGol-SR (and no xyloglucan) can be used as a dot blot to test for the activity of the glycosylhydrolases ($\alpha$-xylosidase, $\beta$-glucosidase and $\beta$-galactosidase) that together catalyse the exo-hydrolysis of XLLGol. The assay is conducted in a manner similar to that described in 3(a), above, except that: in step (iv) a solvent is selected (e.g. 90% ethanol) that removes from the paper the hydrolysis products of XLLGol-SR below a certain size but not XLLGol-SR itself; and step (v) involves no further solvents, but only drying. Activity of the relevant glycosylhydrolase enzymes thus yields non-fluorescent spots on a fluorescing paper background.

The method described above for preparing XLLGol-SR is readily adaptable to form a generally valuable means of preparing fluorscently (or otherwise) labelled reducing oligosaccharides or polysaccharides. Such labelled saccharides (e.g. oligo-SRs) can be used:

in diverse enzymes assays for endo- and exo-glycosylhydrolases and transglycosylases, including those involved in starch metabolism;

in detecting, separating and characterising oligosaccharides of interest by HPLC or TLC in combination with the use of pure glycosylhydrolases, the oligo-SRs acting as authentic markers;

as a probe which is suitable for application, with or without added unlabelled xyloglucan, to plant tissue in order to map the distribution of XET activity histochemically, by use of fluorescence microscopy.

O-Glycosyl-1-amino-1-deoxy-alditols and/or O-oligoglycosyl-1-amino-1-deoxy-alditols can be prepared by the method (reductive amination) described, starting from any reducing oligosaccharide. Analogous products are obtained from oligosaccharides in which the reducing terminus is a modified sugar; for example, in the case of an oligosaccharide whose reducing terminus is a hexuronic acid moiety, the reaction product is an O-oligoglycosyl-6-amino-6-deoxy-aldonic acid or its lactone. Any of these products of the reductive amination reaction can be detected via their amino group, e.g. by staining with ninhydrin, and can themselves be utilised for diverse purposes including for the chromatographic and electrophoretic analysis of oligosaccharides;

as modulators of enzyme action.

REFERENCES

[1] Fry S C, Smith R C, Renwick K F, Martin D J, Hodge S K, Matthews K J (1992): Xyloglucan endotransglycosylase, a new wall-loosening enzyme activity from plants. *Biochemical Journal* 282: 821–828.

[2] Fry S C, York W S, Albersheim P, Darvill A, Hayashi T, Joseleau J-P, Kato Y, Lorences E P, Maclachlan G A, McNeil M, Mort A J, Reid J S G, Seitz H U, Selvendran R R, Voragen A G J, White A R (1993): An unambiguous nomenclature for xyloglucan-derived oligosaccharides. *Physiologia Plantarum* 89: 1–3

What is claimed is:

1. A method of detecting the presence of a transglycosylase enzyme in a sample under test, the method comprising the steps of:

impregnating a suitable base material with a marker substance comprising an oligosaccharide selected from the group consisting of an O-glycosyl-1-amino-1-deoxy-alditol and an O-oligoglycosyl-1-amino-1-deoxy-alditol, that interacts with the transglycosylase enzyme, the marker substance being labeled in a detectable manner, the base material being further impregnated with an unlabeled co-substrate for the transglycosylase enzyme, the marker substance having a substantially lesser affinity for the base material than the product of the interaction of the transglycosylase enzyme with the marker substance and the co-substrate, bringing the impregnated base material into contact with the sample under test, to permit the labeled marker substance to interact with any transglycosylase enzyme present in the sample, removing unreacted labeled marker substance with a suitable solvent, and detecting the presence of labeled marker substance remaining on said base material, to give an indication of the presence or absence of transglycosylase enzyme.

2. A method according to claim 1, suitable for:
(a) conducting dot-blot assays of aqueous solutions (i) for the activity of a transglycosylase enzyme or (ii) for the presence of substances that promote or inhibit transglycosylase activity;
(b) conducting tissue-printing to study the distribution of transglycosylase activity within plant tissue; or
(c) conducting blots of gel electrophoretograms to study the distribution of transglycosylase activity on zymograms.

3. A method according to claim 1, for the detection of xyloglucan endotransglycosylase (XET), the marker substance being an oligosaccharide derived from xyloglucan, and the co-substrate being xyloglucan.

4. A method according to claim 1, wherein the marker substance is labeled fluorescently, radioactively or by being colored.

5. A method according to claim 1, wherein the marker substance is an oligosaccharidyl-1-amino-1-deoxy-alditol (OAD).

6. A method according to claim 5, wherein the OAD is a derivative of 4-O-[4-O-[4-O-[6-O-α-D-Xylopyranosyl-β-D-glucopyranosyl]-6-O-(2-O-β-D-galactopyranosyl)-α-D-xylopyranosyl-β-D-glucopyranosyl]-6-O-(2-O-β-D-galactopyranosyl)-α-D-xylopyranosyl-β-D-glucopyranosyl]-D-glucose (XLLG).

7. A method according to claim 1, wherein the marker substance is labeled with lissamine rhodamine sulphonyl chloride.

8. A kit for assaying xyloglucan endotransglycosylase comprising a base material impregnated with an oligosaccharide selected from the group consisting of an O-glycosyl-1-amino-1-deoxy-alditol and an O-oligoglycosyl-1-amino-1-deoxy-alditol.

9. An amino deoxyalditol derivative of 4-O-[4-O-[4-O-[6-O-α-D-Xylopyranosyl-β-D-glucopyranosyl]6-O-(2-O-β-D-galactopyranosyl)-α-D-xylopyranosyl-β-D-glucopyranosyl]-6-O-(2-O-β-D-galactopyranosyl)-α-D-Xylopyranosyl-β-D-glucopyranosyl]-D-glucose.

* * * * *